(12) United States Patent
Imran

(10) Patent No.: US 9,320,431 B2
(45) Date of Patent: Apr. 26, 2016

(54) DEVICE, SYSTEM AND METHOD FOR MONITORING AND COMMUNICATING BIOMETRIC DATA OF A DIVER

(75) Inventor: Mir Imran, Los Altos Hills, CA (US)

(73) Assignee: InCube Labs, LLC, San Jose, CA (US)

(*) Notice: Subject to any disclaimer, the term of this patent is extended or adjusted under 35 U.S.C. 154(b) by 1111 days.

(21) Appl. No.: 13/237,912

(22) Filed: Sep. 20, 2011

(65) Prior Publication Data

US 2012/0065486 A1   Mar. 15, 2012

Related U.S. Application Data

(63) Continuation-in-part of application No. 13/231,881, filed on Sep. 13, 2011.

(60) Provisional application No. 61/384,612, filed on Sep. 20, 2010, provisional application No. 61/382,438, filed on Sep. 13, 2010, provisional application No. 61/384,612, filed on Sep. 20, 2010.

(51) Int. Cl.
| | |
|---|---|
| *A61B 5/1455* | (2006.01) |
| *A61B 5/00* | (2006.01) |
| *A61B 5/0205* | (2006.01) |
| *B63C 11/02* | (2006.01) |
| *B63C 11/26* | (2006.01) |

(Continued)

(52) U.S. Cl.
CPC .............. *A61B 5/0002* (2013.01); *A61B 5/0205* (2013.01); *A61B 5/7228* (2013.01); *B63C 11/02* (2013.01); *B63C 11/26* (2013.01); *A61B 5/021* (2013.01); *A61B 5/024* (2013.01); *A61B 5/0816* (2013.01); *A61B 5/14551* (2013.01); *A61B 2560/0247* (2013.01); *B63B 22/00* (2013.01); *B63B 35/00* (2013.01); *B63B 2035/007* (2013.01)

(58) Field of Classification Search
CPC ............... A61B 5/1455; A61B 5/0002; A61B 5/14551; A61B 5/14552; A61B 5/681; A61B 5/7228; A61B 5/7278; A61B 2560/0242
USPC .................................. 600/310, 322, 323, 336
See application file for complete search history.

(56) References Cited

U.S. PATENT DOCUMENTS

| | | | |
|---|---|---|---|
| 4,232,381 A | 11/1980 | Rennick et al. | |
| 4,330,895 A | 5/1982 | Putman et al. | |

(Continued)

FOREIGN PATENT DOCUMENTS

| | | |
|---|---|---|
| EP | 2075189 A1 | 7/2009 |
| FR | 2655834 | 6/1991 |

(Continued)

OTHER PUBLICATIONS

International Search Report and Written Opinion issued in related International Application PCT/US2011/051473, dated May 21, 2012.

(Continued)

*Primary Examiner* — Eric Winakur
(74) *Attorney, Agent, or Firm* — Mahamedi Paradice LLP

(57) ABSTRACT

A system and method for monitoring biometric data of a diver and signaling those data from a first communication device to other communication devices, e.g., those of other divers, on a ship or buoy. A signal generated from a device of the diver can generate a diver identifier, an indication of a stress state of the diver and the diver's location.

22 Claims, 8 Drawing Sheets

(51) Int. Cl.
  *A61B 5/021* (2006.01)
  *A61B 5/024* (2006.01)
  *A61B 5/08* (2006.01)
  *B63B 22/00* (2006.01)
  *B63B 35/00* (2006.01)

(56) References Cited

U.S. PATENT DOCUMENTS

| | | | |
|---|---|---|---|
| 4,837,578 A | 6/1989 | Gammell | |
| 5,176,552 A | 1/1993 | Kuboyama et al. | |
| 5,331,602 A | 7/1994 | McLaren | |
| 5,577,942 A | 11/1996 | Juselis | |
| 5,664,636 A | 9/1997 | Ikuma et al. | |
| 5,712,447 A | 1/1998 | Hanson | |
| 5,717,657 A | 2/1998 | Ruffa | |
| 5,784,339 A * | 7/1998 | Woodsum et al. | 367/134 |
| 6,382,022 B1 | 5/2002 | Martinez et al. | |
| 6,402,690 B1 * | 6/2002 | Rhee et al. | 600/310 |
| 6,577,932 B1 | 6/2003 | Van Beurden et al. | |
| 6,854,410 B1 | 2/2005 | King et al. | |
| 6,856,578 B2 | 2/2005 | Magine et al. | |
| 7,642,919 B2 | 1/2010 | Leal et al. | |
| 2004/0090865 A1 | 5/2004 | Davies et al. | |
| 2004/0174259 A1 | 9/2004 | Peel et al. | |
| 2008/0162042 A1 | 7/2008 | Huber et al. | |
| 2009/0060353 A1 | 3/2009 | Saisan et al. | |
| 2009/0095208 A1 | 4/2009 | Cardoza et al. | |
| 2010/0091612 A1 | 4/2010 | Skrobanek et al. | |

FOREIGN PATENT DOCUMENTS

| | | |
|---|---|---|
| GB | 2390903 | 1/2004 |
| JP | 61-120980 A | 6/1986 |
| JP | 2006-021566 A | 1/2006 |
| WO | WO 2004/019776 | 3/2004 |

OTHER PUBLICATIONS

EP Extended Search Report dated Jul. 17, 2014 in EP 11825827.6.
International Search Report and Written Opinion as issued in corresponding international application PCT/US2011/052429, dated Apr. 24, 2012.
Non-Final Office Action in U.S. Appl. No. 13/231,881, mailed Oct. 1, 2013.
First Examination report in European Application No. 11827392.9, mailed Apr. 16, 2014.
Notice of Allowance in U.S. Appl. No. 13/231,881, mailed Apr. 14, 2014.

* cited by examiner

DEVICE, SYSTEM AND METHOD FOR MONITORING AND COMMUNICATING BIOMETRIC DATA OF A DIVER

RELATED APPLICATIONS

This application claims priority to provisional U.S. patent application Ser. No. 61/384,612, filed Sep. 20, 2010, which is hereby incorporated by reference in its entirety for all purposes.

This application is a continuation-in-part of U.S. patent application Ser. No. 13/231,881, filed Sep. 13, 2011; which claims benefit of priority to (i) provisional U.S. patent application No. 61/382,438, filed Sep. 13, 2010, and to (ii) provisional U.S. patent application No. 61/384,612, filed Sep. 20, 2010; all of the aforementioned priority applications being hereby incorporated by reference in their respective entireties for all purposes.

FIELD OF THE INVENTION

Embodiments described herein relate to a system for monitoring a diver. More specifically, embodiments described herein relate to a system for monitoring and communicating biometric data of a diver such as heart rate or blood oxygen saturation.

BACKGROUND

SCUBA (Self-Contained Underwater Breathing Apparatus) diving is becoming an increasingly popular activity both for recreation and in various industrial applications (e.g., underwater welding, oil rig repair, salvage, etc.). There are a number of health risks associated with SCUBA diving due to the underwater environment in which divers operate and the subsequent effect on their physiology. These include hypoxia, hypercapnia, embolism, the "bends", nitrogen narcosis, pressure induced arrhythmias and lung expansion injury. Many of these conditions can occur or enter a precursor state with little or no apparent warning to the diver. While divers can be trained to recognize the symptoms, they often don't or choose not to. While there are portable devices the diver can take with them to monitor physiological indicators of these symptoms, the diver often is not vigilant enough in monitoring the indicators (being preoccupied with the dive), the conditions develop too quickly or they are not provided with the indicators for particular conditions, such as hypoxia, in a form they can readily discern. What is needed is a system for monitoring a diver's biometric data and transmitting that data so that indicators of physiological distress and other conditions can be analyzed by others without distraction. What is also needed is a system for monitoring particular biometric data including data more indicative of particular adverse physiological conditions.

DETAILED DESCRIPTION

Figure 1A:
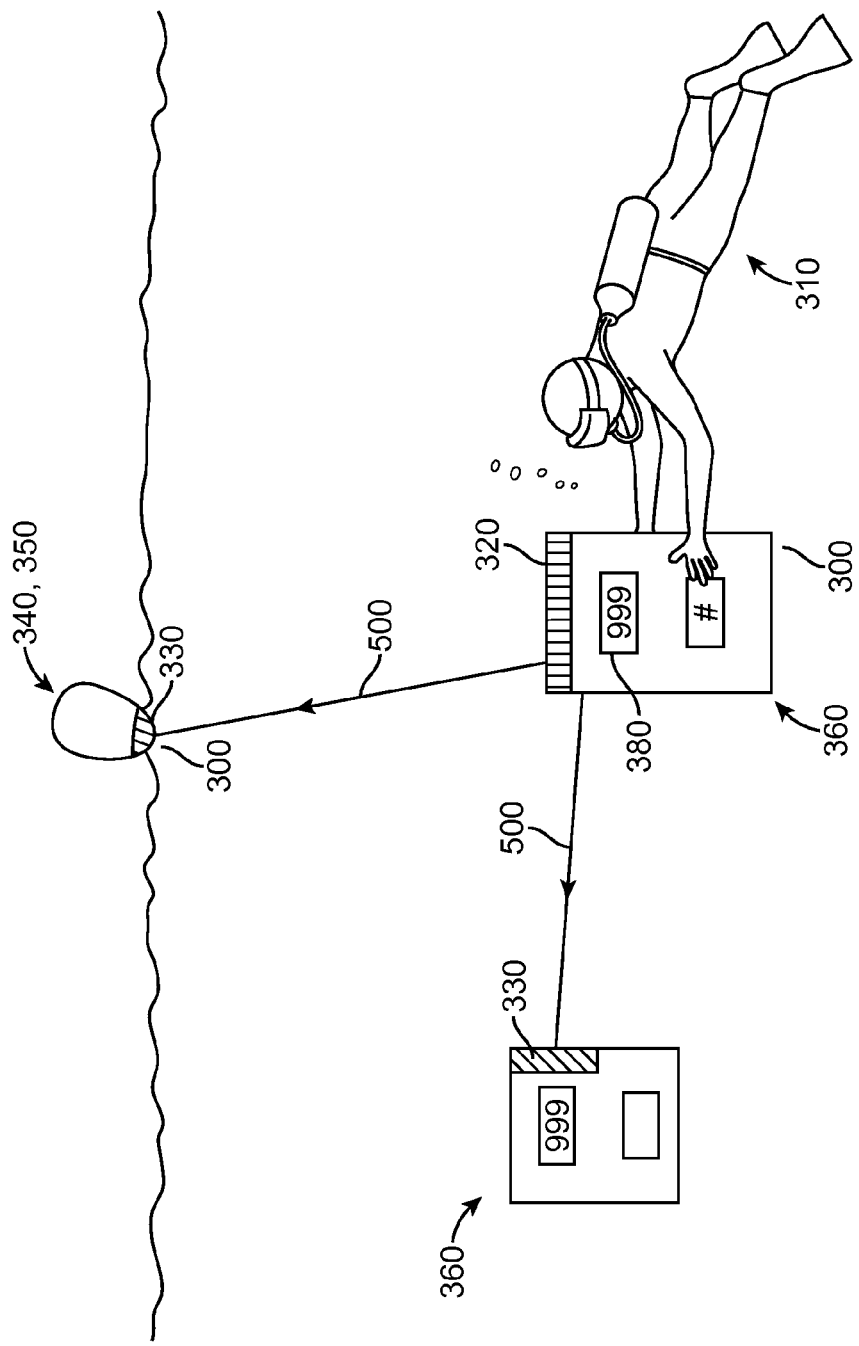
FIG. 1A illustrates an embodiment of the biometric data communication system.

Embodiments described herein provide a system and method for monitoring various biometric data (e.g., heart rate, blood gases, etc.) of a diver and signaling the data from a first communication device which is underwater to another communication device on a surface platform such as a floating buoy. In many embodiments, the communication device can be provided by a mobile or portable device (e.g., handheld device such as cellular messaging/telephony or personal digital assistant) which can include a processor, display and user input device such as a touch screen. The communication device can include (inherently or by way of accessory functionality) an acoustical transducer, for example, an ultrasonic transducer comprising a piezoelectric material. The processor is configured to monitor various physiological data including heart rate, respiration rate, blood pressure, blood oxygen saturation and other blood gas measurements. The communication device may also implement one or more algorithms which use such data to determine if the diver is in a state of physiologic stress (e.g. such as that caused by blood oxygen levels or outgassing of nitrogen, causing the "bends") or a state preceding or otherwise predictive of a state of physiological stress.

According to embodiments, when such a state or precursor state of stress is detected, the first communication device communicates information (e.g. notification, message etc.) to one or more other communication devices to allow other individuals (such as those on a dive boat or other monitoring craft or even those onshore) to monitor the diver(s) and/or alert them when it is time to take action (e.g., have the divers ascend and/or provide assistance to the divers).

In one embodiment, the first communication device can send out an acoustical distress signal to the communication device of any other diver in the vicinity when the diver is in a precursor or state of physiologic stress. The signal can include various information including an identifier of the particular diver, the particular state he or she is in and the location of the diver (either absolute and/or in relation to the floating buoy, dive boat or other craft).

Other embodiments provide a device, system and method for (i) measuring or otherwise determining blood oxygen or other blood gas saturation of a diver while he or she is underwater, and then (ii) converting measured/determined data an acoustic signal for transmission to an acoustical communication device. The system can include a watertight monitoring device, which can be a portable or mobile device worn by the diver. The device may be coupled to a sensor device either directly or wirelessly for example, using RF communication. The sensor device can comprise a band or strip worn over an extremity such as a finger or toe. In one implementation, the device has an optical emitter and detector to emit and detect light. Information detected from the sensor can be used to determine, for example, an absorbance which is correlative or otherwise corresponding to a blood oxygen saturation of the diver using oximetry methods known in the art.

Among other variations, the band or strip can be held in place using a clip, clamp, or a resilient sleeve worn over the finger or toe and can also include other configurations for holding the sensor device at a desired location on or adjacent the diver's body. In one embodiment, the sensor device, including the band or strip, may be incorporated into a section of the finger covering of a glove worn over the diver's hand.

In one embodiment, the monitoring device can include an RF communication device for receiving an input from the sensor device, and a processor configured to control the intensity, duration, frequency or other characteristic of an optical signal from the emitter. The processor may also implement a process for (i) calculating blood saturation levels from the inputted optical signal (e.g., calculation module), (ii) converting the measured blood oxygen saturation or other information into an acoustical signal (e.g., "a signal processing module"), (iii) creating an ID signal used to identify the diver and controlling the transmission of the acoustical signal (e.g., "a communications module") and (iv) monitoring the devices and/or divers.

According to some embodiments, the one or more processors may implement a process or alarm module for determining when the diver's blood oxygen saturation is too low or otherwise indicating that the diver is in a state of distress and a master control module for controlling the functions of one or more of the preceding modules.

Various embodiments described herein use devices that are carried by or with divers. These devices may be made of various design, form factor and/or platform. In some embodiments, the devices are specialty devices, configured logically and structurally for use with divers. In other embodiments, the devices are configured or reconfigured devices having primary or past functionality in the form of messaging, cellular communications (e.g. smart phone) or personal information management (PIM). In some embodiments, the devices are accessorized to include components with functionality as described. For example, attachment modules to existing handsets may carry components as described by some embodiments. Still further, the devices may be carried as handsets or worn by the divers (e.g. wrist watch, computerized necklace, wristband or headband etc.).

Figure 1B:
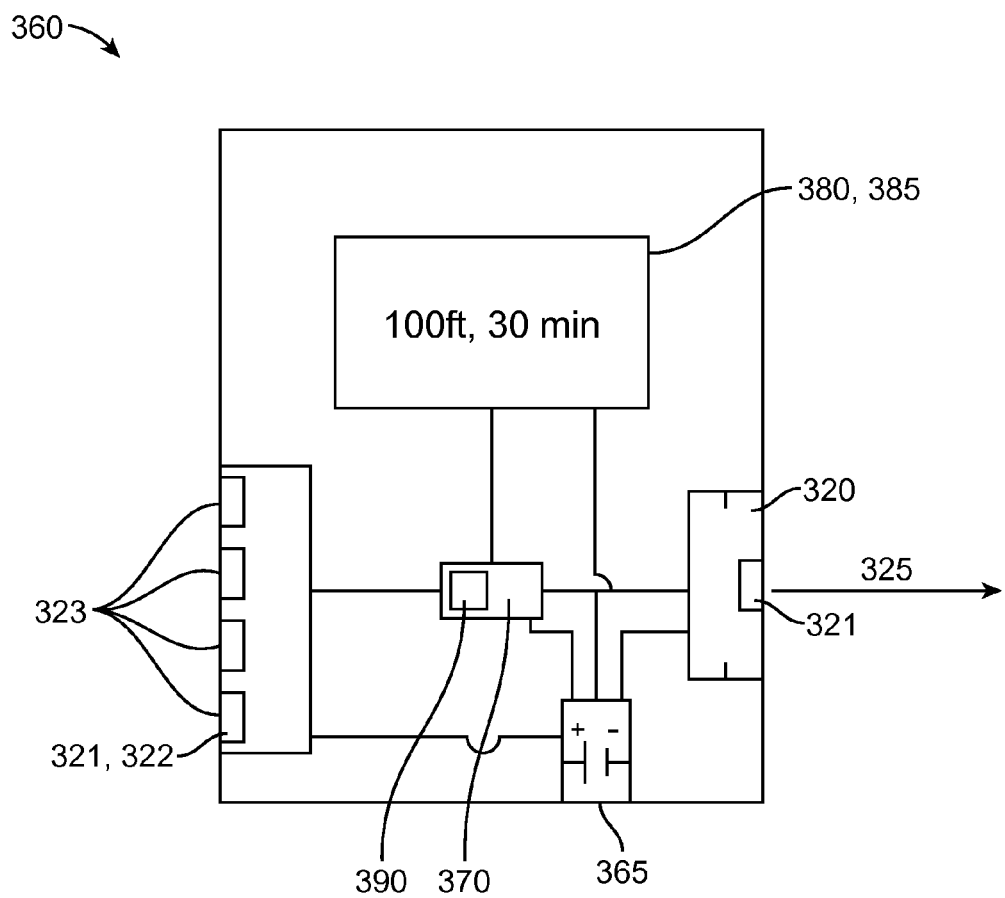
FIG. 1B illustrates an embodiment of a portable underwater monitoring device such as a PDA-like device.
Figure 2:
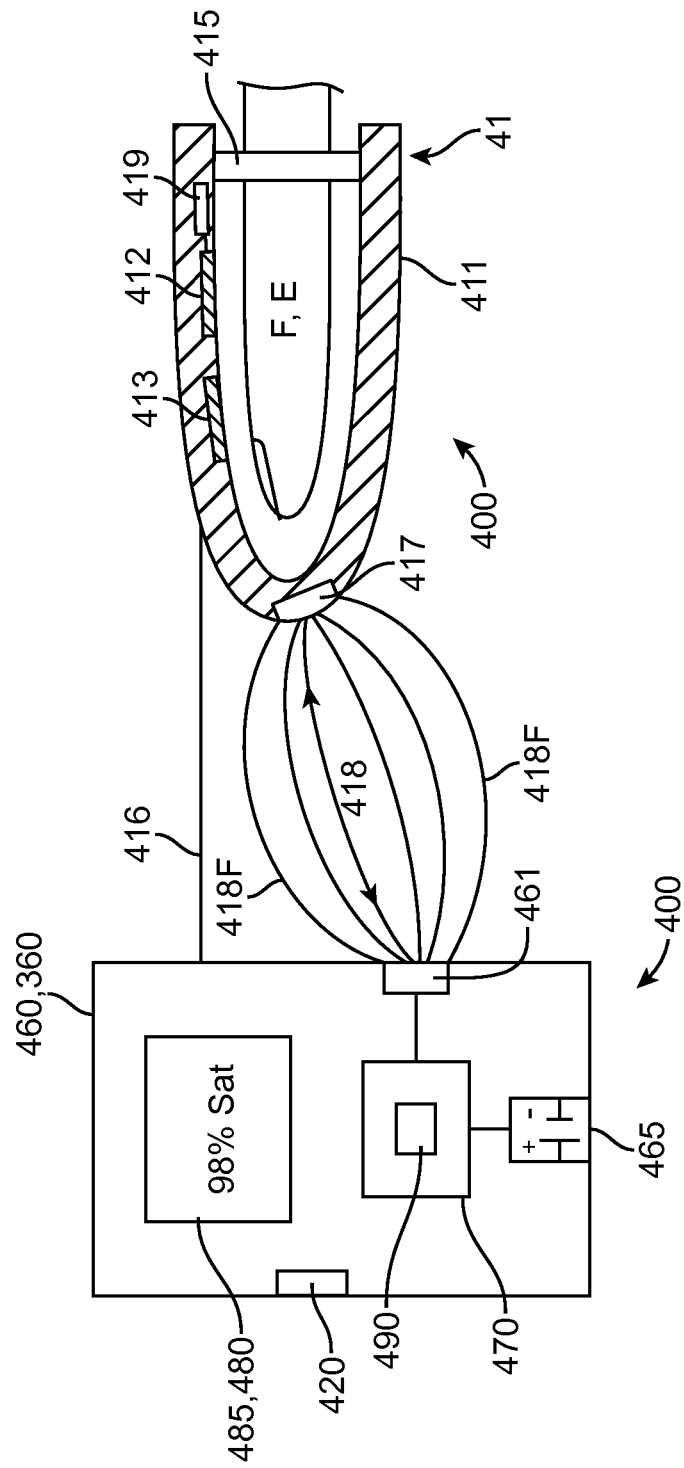
FIG. 2 is a lateral view of an embodiment of a system including a sensor device for optically measuring blood oxygen or other blood gas saturation of a diver.

As used herein, the terms "acoustic" and "acoustical" are used interchangeably. Referring now to FIGS. 1A-1B, various embodiments provide a system 300 and methods for monitoring various biometric data (e.g., heart rate, blood gases, etc.) of a diver 310 and signaling those measurements from a first communication device 320 worn or carried by the diver 310 to another communication device 330 which may be underwater or positioned on a surface platform 340, which in many embodiments, corresponds to a floating buoy 350. In various embodiments, buoy 350 can be a self-propelled buoy 350 having a propulsion control system for staying within an effective communication range of diver 310. Further description of various embodiments of self propelled buoys is found in U.S. Provisional Patent Application Ser. No. 61/382,438 and U.S. patent application Ser. No. 13/231,881 which are both fully incorporated by referenced herein. In many embodiments, the first communication device 320 can be incorporated into a watertight portable monitoring device 360. Portable monitoring device 360 will typically comprise a PDA like device 360 that is worn or carried by diver 310. Device 360 may also comprise, or be integrated into, a dive watch, dive computer or other device or equipment carried by the diver, e.g., a flash light, depth gauge, regulator, etc. For ease of discussion, device 360 will now be referred to as PDA 360; however, other embodiments are equally applicable. PDA 360 includes a processor 370, display 380, user input means 385, and an electrical power source 365. Power source 365 may correspond to a portable battery, such as a lithium or lithium ion battery, or other battery chemistry known in the art. Display mean 85 may correspond to a touch screen which may be separate or integral with display 380. Processor 370 includes one or more modules 390 for controlling various operations of device 360 including those of communication device 320 as will be explained further herein.

Communication devices 320 and 330 can comprise one or more acoustical transducers 321 which transmit and/or receive acoustical energy at a selected frequency or range of frequencies. Acoustical transducers 321 may correspond to one or more ultrasonic transducers 322 which can comprise various piezoelectric materials such as piezo-electric ceramic materials. The particular acoustical transducer 321 and acoustical frequency can be selected based on the desired acoustical transmission range, acoustical sensitivity, bandwidth, maximum diving depth, temperature and salinity conditions, and related parameters. In various embodiments, the acoustical frequencies used by devices 320 and 330 (or other similar device) can be in the range of about 20-150 kHz, more specifically, in the range of about 50-125 kHz and still more specifically, in the range of about 70-100 kHz. Other ranges are also contemplated. The specific range can be selected depending upon one or more factors such as the expected ambient conditions (e.g. temperature), expected depth, desired bandwidth of data, and desired communication range. Also, acoustical transducers 321 may be configured as both acoustical transmitters and receivers so as to send and receive acoustical signals. In many embodiments, transducers 321 can be arranged as an array 323 of transducers which may include a phased array formation. Array 323 can be configured to optimize one or more of the transmission range, sensitivity, and bandwidth of communication device 320. Larger arrays 323 (e.g., a greater number of transducers, and/or spread out over a larger area) can be used to increase sensitivity and transmission distance. In particular embodiments, the communication devices 320 from multiple divers 310 can be used to form an array 323 having increased sensitivity and transmission range.

The processor 370 will typically correspond to one or more microprocessors known in the art and can be selected for increased durability, fault tolerance, and pressure resistance for underwater operation, using various MIL-SPEC criteria known in the military/naval equipment arts. Processor 370 will typically include one or more modules or algorithms 390 for computing, monitoring, and communicating various physiological data of diver 310 including for example, heart rate, respiration rate, blood pressure, blood oxygen saturation and other blood gas measurements (e.g., blood nitrogen). It may also include other modules 390 which use such data to determine if the diver is in a state of physiologic stress (e.g., such as that caused by low blood oxygen levels, (e.g., "hypoxia") or out gassing of nitrogen, causing the "bends") or a precursor state which precedes or is otherwise predictive of a state of physiological stress. When such a stress state or precursor state of stress is detected, it may be communicated by the first communication device 320 to the second communicative device 330 to allow other individuals (such as those on the dive boat or even those onshore) to monitor the diver(s) and alert them when it is time to ascend and/or if diver requires assistance.

In one embodiment, the first communication device 320 can send out an acoustical distress signal 325 when the diver is in a precursor and/or state of physiologic stress. Signal 325 can include various information including an identifier of the particular diver, the particular state the diver is in, and the location of the diver. The signal 325 can be configured to reach not only communication device 330 on the water surface (such as that in the buoy, dive boat or monitoring ship) but also the communication device 330 of any other diver in the vicinity. In particular embodiments, signal 325 may be sent at a different acoustical frequency or range of frequencies from that normally used by communication devices 320 and 330 such that: i) persons or equipment monitoring communications from the devices will immediately know that there is a diver in a distress; and ii) there is little or no interference from other acoustical communication between devices 320 and 330. Further, signal 325 may also include a priority or over-ride signal sent at the beginning of 325 which puts all other communication devices 330 into a listening mode for a select period of time (e.g., up to one minute or longer) so as to assure no interference from signals sent by other devices 330 and thus improve the ability of other devices 330 for detecting distress signal 325 as well as the transmission range of signal 325 (e.g., by improving its signal to noise ratio). The priority signal can be sent at a different frequency or range of frequencies than that normally used by devices 320 and 330.

Referring now to FIGS. 2 and 3A-5 other embodiments also provide a device 410, system 400 and method for measuring blood oxygen saturation (or other blood gas) of a diver 310 while he or she is underwater and then convert that measurement into an acoustic signal for transmission to an acoustical communication device described herein. System 400 can include a watertight monitoring device 460 such as a PDA-like device 460 (herein PDA 460) worn or carried by the diver 310 that is coupled to a sensor device 410. PDA 460 may be one in the same as PDA 360 and in many embodiments may comprise or otherwise be incorporated into a dive watch or like device that is worn on the diver's wrist or arm. PDA 460 may be coupled to sensor device 410 either directly for example, using a connector 416 (such as a cable or wire) or wirelessly for example, using magnetic communication as is described below.

Figure 3A:
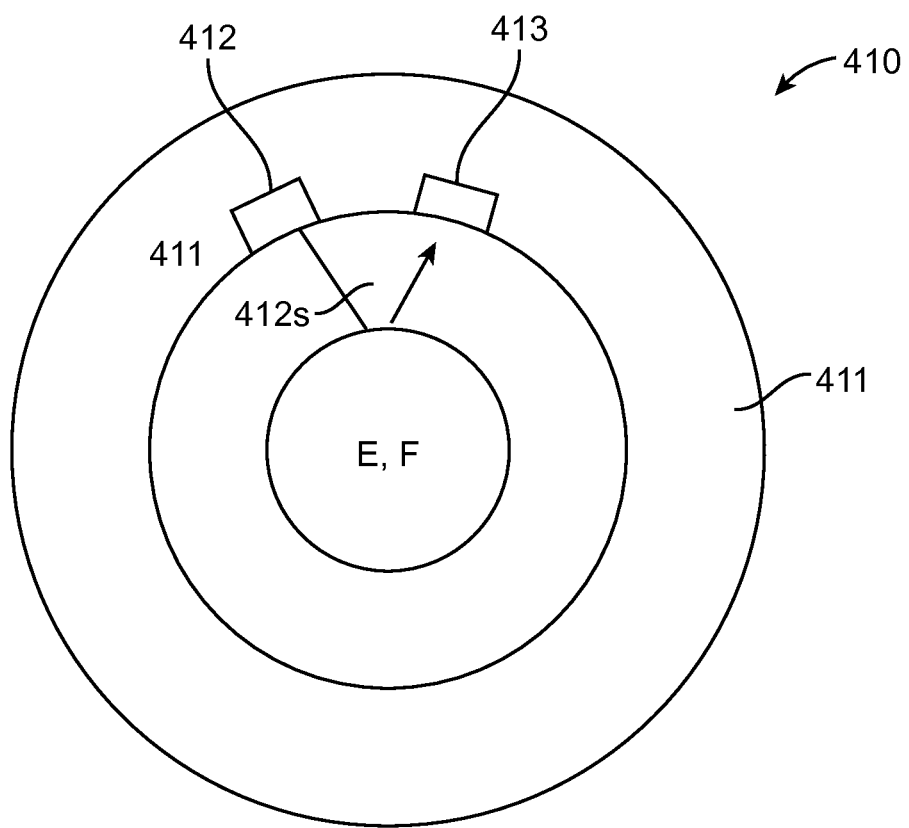
FIG. 3A is a cross sectional view of an embodiment of the sensor device having an elastic band with the emitter and detector configured for reflectance oximetry.
Figure 3B:
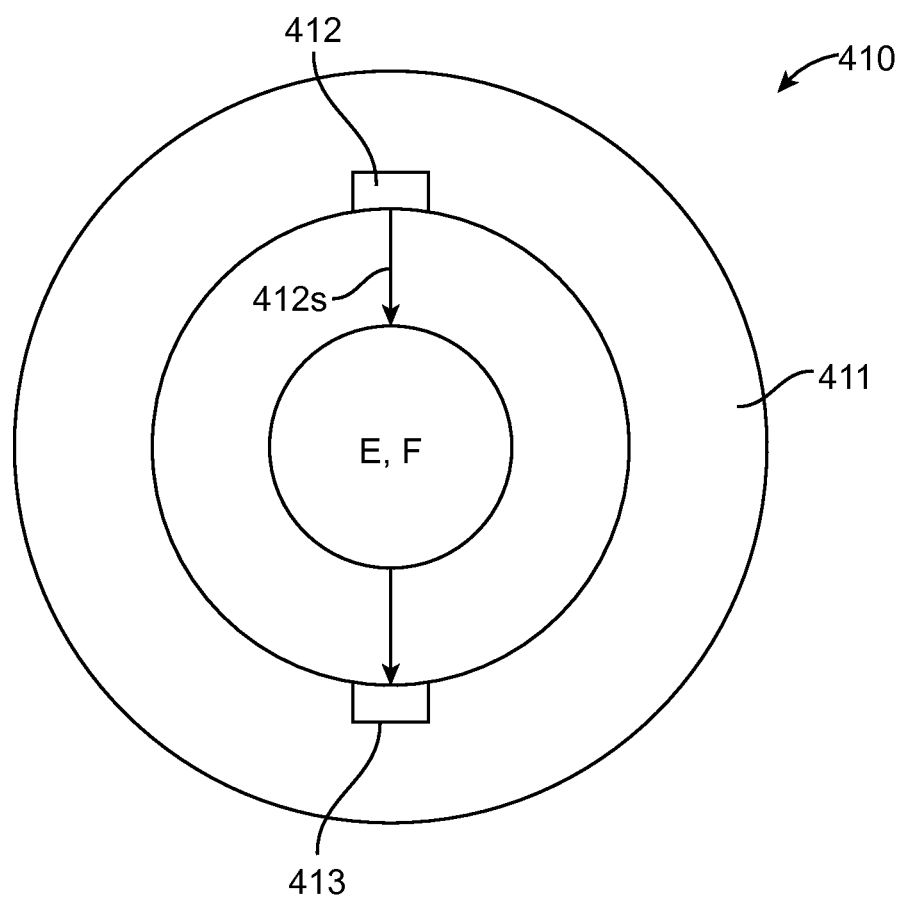
FIG. 3B is a cross sectional view of an embodiment of the sensor device having an elastic band with the emitter and detector configured for absorbance oximetry.

Sensor device 410 can comprise a support layer 411, an optical emitter 412 and optical detector 413 and an electrical power source 419 such as a lithium button battery or other miniature battery known in the art. Support layer 411 may correspond to a band, strip or cuff 411 that is worn over a site on the diver's skin, typically, an extremity E such as a finger F or toe. For ease of discussion, support layer 411 will now be referred to as a band 411. Band 411 has an optical emitter 412 (which may correspond to one more LED's of the same or different wavelengths) and optical detector 413 (which may correspond to one or more Photodiodes) that are selected and arranged to emit and detect light of at least one wavelength having an absorbance which is correlative or otherwise corresponding to a blood oxygen saturation level (or other blood gas) of the diver using oximetry methods known in the art. In particular embodiments, the wavelength can include at least a first and second wavelength with larger numbers considered. Additionally, the emitted light can also include a reference signal having an absorbance which is only minimally effected by the oxygen saturation level of the divers blood. The emitter and detector 412 and 413 are waterproofed and selected and configured to withstand the pressures of the dive. Emitter and detector 412 and 413 can be configured for reflectance type or absorbance type oximetry. For embodiments using reflectance type oximetry, the emitter(s) and detector(s) are placed proximate each other on the same side of the diver's skin as is shown in the embodiment of FIG. 3A. For embodiments using absorbance type oximetry, the emitter and detector are placed on opposite sides of the skin on an area of the skin that has good blood flow and fairly translucent (such as the finger or earlobe) as is shown in the embodiment of FIG. 3B. For either embodiment, the intensity and other optical characteristic of the light emitted by emitter 412 can be modulated or otherwise adjusted for underwater conditions, such as depth, water temperature, or optical property of the water the diver is in. For example, the intensity of the emitted light can be modulated with respect to the diver's depth (measured e.g., by means of an electronic depth gauge that is operatively coupled to device 410 and/or PDA 460). Higher intensities can be used for deeper depths due to fact that the higher water pressures at deeper depths may cause blood normally present in the upper layers of the skin to be forced away from the skin surface into deeper tissue. Thus a stronger intensity may be needed to penetrate deeper into the skin and subjacent tissue where sufficient blood is present to make an oximetry measurement. Correlations can be developed between required signal strength and diving depth using known mathematical modeling and/or laboratory testing and models (e.g., least squares, cubit spline). In various embodiments, the intensity of light from emitter 412 can be adjusted linearly, logarithmically or other manner with respect to depth (e.g., in a first or second order manner). A similar situation may occur for colder water temperatures, where, due to vasoconstriction of the skin, from colder temperatures, blood is forced away from the skin, requiring higher intensities. Also higher intensities can be used to compensate for losses in intensity of the incident or reflected/transmitted light from the skin due to the presence of water and various particulate matter in the water (e.g., due to scattering, reflectance etc.). In this latter case, a calibration signal may be sent to compensate for the presence of water, e.g., before emitter 412 emits an optical signal 412s used for measurement of blood oxygen saturation. Alternatively, a dual beam approach can be used for optical signal 412s with one beam directed at the diver's skin the other into any water near the diver's skin.

Figure 4:
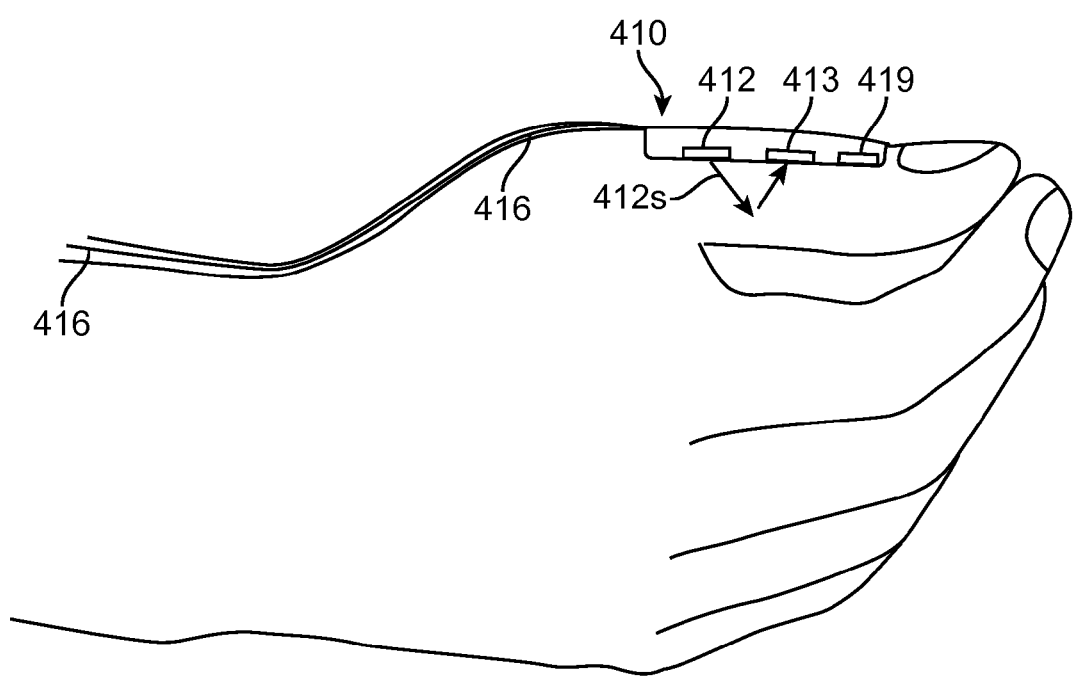
FIG. 4 is a lateral view showing an embodiment of a sensor device incorporated into a diver's glove.

The emitter and detector 412 and 413 can be integral or otherwise attached to band 411 such that they face into the skin surface. They may also be recessed within band 411 so that they will be pressed into the skin by embodiments having a resilient/elastic band 411 and/or the force of surrounding water pressure and thus improve or optimize the watertight seal between band 411 and the skin as they do not create any gaps or protuberances between the band and the diver's skin. Band 411 is configured to form a watertight seal with the particular extremity (e.g., appendage) it is worn over. Accordingly, band 411 can be held in place using an attachment feature 415 such as a clamp, clip, VELCRO area or an elastic sleeve worn over band 411 at least a portion of the finger or other extremity E. Band 411 itself may comprise an elastic sleeve worn over the finger or other extremity E. In one embodiment, the sensor device 410 including the band 411 may be incorporated into a section of the finger covering of a glove worn over the diver's hand as is shown in the embodiment of FIG. 4. Other embodiments contemplate a number of configurations for band 411 so that it may place position emitter and detector 412 and 413 or other sensor device 410 on or adjacent the diver's body.

The PDA device 460, can include an acoustic communication device 420, a magnetic communication device 461 for receiving an input from the sensor device 410, a processor 470, display 480 a user input means 485 such as a touch screen and a power source 465 for powering various components of the PDA as well as the sensor device 410. In one or more embodiments power source 465 may correspond to a chemical battery such as lithium, lithium ion, or other battery chemistry known in the art. Magnetic communication device 461 is configured for receiving an input from magnetic communication device 417, and a microprocessor 470 (which can have similar properties as microprocessor 370) having one or more modules 490 for performing one or more operations relating to the calculation, processing and communication of various biometric data.

Figure 5:
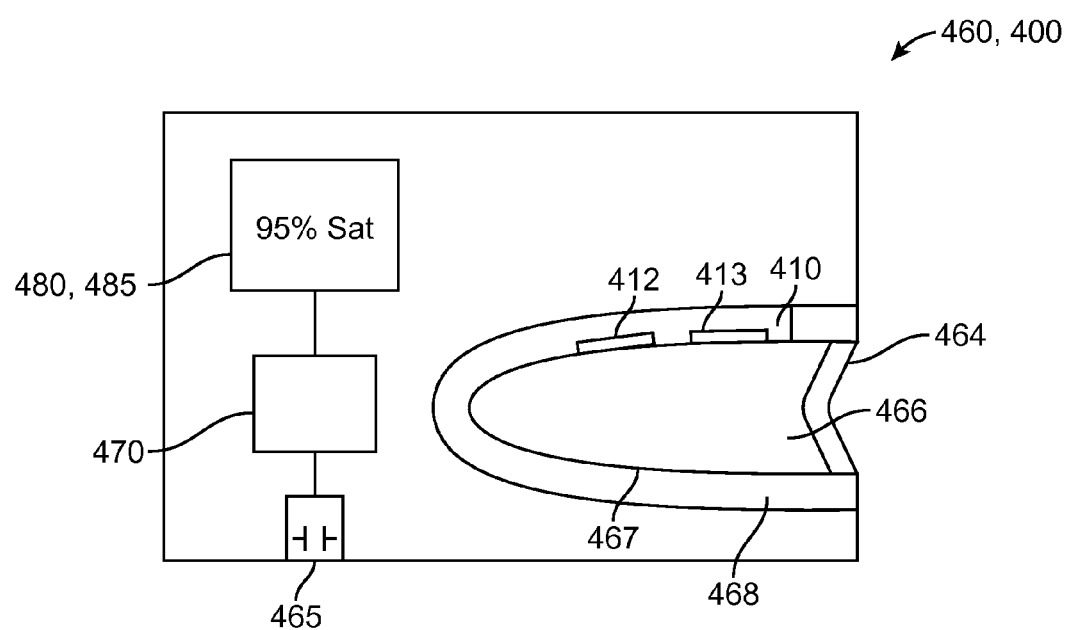
FIG. 5 is a lateral view showing an embodiment of a monitoring device having an internal sensor device for optically measuring blood oxygen or other blood gas saturation of a diver.

In an alternative or additional embodiment, PDA 460 may also include an internally based sensor device 410 comprising an internal compartment or chamber 466 having emitter and detector 412 and 413 and configured for insertion of the diver's finger as is shown in the embodiment of FIG. 5. Chamber 466 will typically include a gasket or other water tight flexible seal 469 attached to the wall of the PDA through which the diver inserts their finger. The internal wall 467 of chamber 466 may comprise a compressible sealing liner 468, such as an elastomer (silicone, polyurethane, etc.), that is conformal to the contour of the diver's finger. The internal diameter of chamber 466 with sealing liner 468 in place is configured such that the sealing liner compresses against the diver's finger and, in this way, assures that the diver's skin is flush against emitter and detector 412 and 413 and eliminating or minimizing any water between the diver's skin and the emitter and detector.

For embodiments of system 400 using magnetic communication, sensor device 410 and PDA 460 can each include magnetic communication devices (also referred to as transceivers) 417 and 461 respectively for sending and receiving a magnetic signal 418. Such devices can comprise a multichip (or hybrid chip) coupled to a magnetic coil. The multichip can be configured to function both as a transmitter and receiver and typically comprises a macro controller chip, op-amps, eproms and other electronic circuits. The antenna coil is tuned to the transmission/carrier frequency and can range from 5 kHz to about 150 kHz, with an preferred range of 30 to 50 kHz and a specific example of about 38 kHz. The multichip generates a signal 418 in the form of a magnetic field 418F which is transmitted and received by the antenna coils. The magnetic field has a strength which falls off by the square of the distance. The effective transmission distance between the devices is a function of transmission power, receiver noise, and sensitivity. The transmission is encoded and modulated, typically in a pulse period or other fashion so as to conserve power. In the receiver mode, the multichip amplifies and decodes the pulse position pulsed data. Transmission bursts may occur at regular intervals, for example, every 5 seconds. After receiving and decoding a valid burst, the receiver shuts down, conserving power, and only wakes up just prior to when the next burst is expected. In this way, transmitter and receiver power may be minimized or otherwise reduced.

Figure 6:
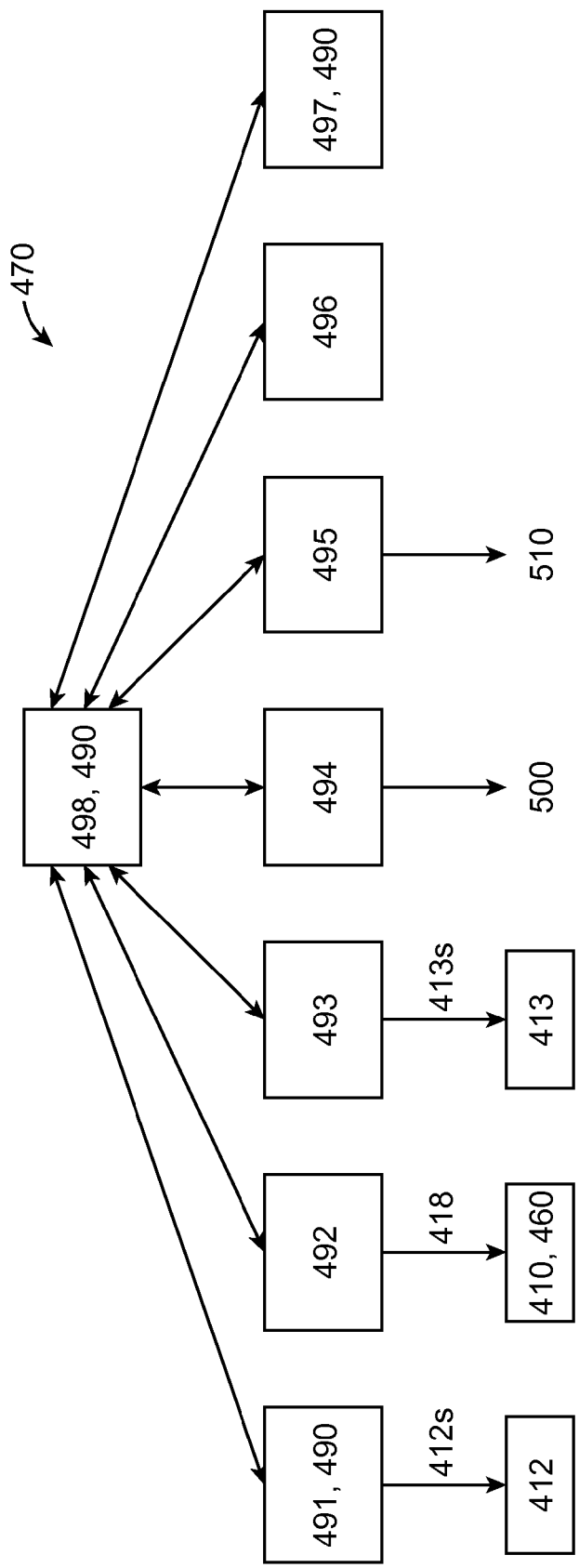
FIG. 6 is a block diagram showing a configuration of various modules operating on an embodiment of the monitoring device processor.

As described above, processor 470 can include a variety of modules or algorithms 490 for controlling various functions of system 400. Referring now to FIG. 6, in various embodiments, modules 490 can include one or more of an optical control module 491 for controlling the intensity, duration, frequency or other characteristic of an optical signal 412s emitted from emitter 412, a magnetic communication module, for controlling embodiments of system 400 employing magnetic communication (e.g., using a signal 418) between sensor device 410 and PDA 460, a calculation module 493 for calculating blood oxygen (or other blood gas) saturation levels using a signal 413s received from detector 413, a signal processing module 494 for converting the measured blood oxygen saturation or other information into an acoustical signal 500, an identifier module 495 for creating an ID signal 510 used to identify the diver, a communications module 496 controlling the transmission of the acoustical signal 500 and a monitoring or alarm module 497 for determining when the diver's blood oxygen saturation is too low or otherwise indicating that the diver is in a state of distress and a master control module 498 for integrating and controlling the functions of one or more of the preceding modules.

In use, measurement and communication of blood oxygen saturation by sensor device 410 and system 400 allows the diver (and those monitoring the diver) to be alerted when the diver is at the earliest stages of hypoxia, and/or precursor states of hypoxia. This allows the diver to take various actions, (e.g., going back to the surface, checking their diving gear, adjusting their regulator, communicating with other divers or those on the surface, etc.), before the further onset of hypoxia and potentially any life threatening conditions. It also allows other divers and/or those on the surface to quickly come to the aid of the diver if necessary. Similarly, for embodiments of sensor device 410 configured for measurement of blood nitrogen saturation, the diver or those monitoring the diver may take various appropriate actions before the development of the "bends." In particular embodiments, PDA device 460 can be configured to alert the diver when their blood nitrogen saturation is too high (which increases the conditions likely for development of the bends) and/or there is a threshold decrease, or rate of decrease of blood nitrogen saturation (implying that nitrogen is coming out of solution, a beginning or early event in the development of the bends). Additionally, such measurements may also be used to assist the diver in making their ascent back to the surface. For example, in some embodiments, system 400 (via use of modules 490, display 480 and/or communication device 420) can be configured to assist the diver in making their ascent by providing visual or audio cues or other information to the diver to remain at a particular depth for a particular period of time, and/or to ascend at a particular rate. In this way, the system 400 allows the diver to make a controlled ascent which reduces the likelihood of the development of the bends. In various embodiments, these assist signals can also be sent out concurrent to when the system has determined when the diver is a in a precursor state and/or state of physiological stress, e.g., hypoxia etc.

Conclusion

The foregoing description of various embodiments have been presented for purposes of illustration and description. It is not intended to limit the invention to the precise forms disclosed. Many modifications, variations and refinements will be apparent to practitioners skilled in the art. For example, various embodiments of the monitoring system can be adapted for salt and fresh water environments, as well as deep dives (e.g., 60 to 200 meters) and cold water environments. They may also be adapted for use in closed circuit re-breathers in addition to standard SCUBA equipment. Additionally, they may be adapted for measurement and monitoring of a number of biometric data including a number of blood gases including oxygen, carbon dioxide, nitrogen and helium.

Elements, characteristics, or acts from one embodiment can be readily recombined or substituted with one or more elements, characteristics or acts from other embodiments to form numerous additional embodiments within the scope of the claimed embodiments. Moreover, elements that are shown or described as being combined with other elements, can, in various embodiments, exist as standalone elements. Hence, the scope of the described embodiments is not limited to the specifics of the description, but is instead limited solely by the appended claims.

What is claimed is:

1. A method for monitoring a blood gas saturation level of a diver, the method comprising:
   emitting an optical signal into water near the diver while the diver is underwater;
   detecting the optical signal;
   determining an underwater condition based on the detected optical signal;
   emitting light into the diver's skin at a wavelength having an absorbance associated with the blood gas saturation level, the intensity of the light modulated responsive to at least the determined underwater condition;
   detecting an intensity of a reflected or transmitted light from the diver's skin; and
   determining the blood gas saturation level of the diver utilizing the detected intensity.

2. The method of claim 1, wherein the light is emitted into the skin while the diver is wearing one or more pieces of SCUBA equipment.

3. The method of claim 1, wherein the intensity of the emitted light is further modulated responsive to a depth of the diver.

4. The method of claim 1, wherein the intensity of the emitted light is further modulated responsive to a water temperature.

5. The method of claim 1, wherein the intensity of the emitted light is further modulated responsive to a water salinity.

6. The method of claim 1, wherein the intensity of the emitted light is modulated responsive to a light absorbance of water near the diver's skin.

7. The method of claim 1, wherein the blood gas saturation is a blood oxygen saturation, the method further comprising:
   alerting the diver when the blood oxygen saturation level is at or below a threshold level.

8. The method of claim 7, wherein the threshold level is about 95% saturation.

9. The method of claim 7, wherein the threshold level is about 90% saturation.

10. The method of claim 1, further comprising:
    generating an acoustical signal including information on the blood gas saturation level, the acoustical signal configured to be transmitted underwater; and
    transmitting the acoustical signal from a first communication device proximate the diver to a second communication device.

11. The method of claim 10, wherein the second communication device is positioned at or near the water surface.

12. The method of claim 11, wherein the second communication device is positioned on a buoy.

13. The method of claim 12, wherein the buoy is self-propelled and includes a control system configured to maintain the buoy within an effective communication range of the first communication device.

14. The method of claim 1, further comprising:
    generating a low power magnetic signal including information on the blood gas saturation level, the magnetic signal configured to be transmitted underwater; and
    transmitting the magnetic signal from a first magnetic communication device to a second magnetic communication device.

15. The method of claim 14, wherein the first magnetic communication device is contained in a sensor device positioned near the diver's finger.

16. The method of claim 14, wherein the second magnetic communication device is contained in a dive watch.

17. The method of claim 14, wherein the first magnetic communication device is contained in a sensor device positioned proximate to the diver's finger.

18. The method of claim 14, wherein the first and second magnetic communication devices are positioned within about six inches of each other.

19. The method of claim 14, further comprising:
    converting the lower power magnetic signal into an acoustical signal including information on the blood gas saturation level, the acoustical signal configured to be transmitted underwater; and
    transmitting the acoustical signal from a first acoustical communication device proximate the diver to a second acoustical communication device.

20. The method of claim 1, wherein the condition is an optical property of water near the diver or a particular content of water near the diver.

21. A method for monitoring a blood gas saturation level of a diver, the method comprising:
    emitting an optical signal into water near the diver while the diver is underwater;
    detecting the optical signal;
    determining an underwater condition based on the detected optical signal;
    emitting light into the diver's skin at a wavelength having an absorbance associated with the blood gas saturation level, the intensity of the light modulated responsive to the determined underwater condition and at least one of a depth of the diver or, a water salinity;
    detecting an intensity of a reflected or transmitted light from the diver's skin; and
    determining the blood gas saturation level of the diver utilizing the detected intensity.

22. The method of claim 21, wherein the condition is an optical property of water near the diver or a particular content of water near the diver.

* * * * *